United States Patent
An (10) Patent No.: US 8,746,509 B2
(45) Date of Patent: Jun. 10, 2014

(54) STRUCTURE FOR CONNECTING A MIXING TIP TO AN IMPRESSION CARTRIDGE

(75) Inventor: Im Jun An, Busan (KR)

(73) Assignee: Seil Global Co., Ltd., Busan (KR)

( * ) Notice: Subject to any disclaimer, the term of this patent is extended or adjusted under 35 U.S.C. 154(b) by 446 days.

(21) Appl. No.: 12/820,629

(22) Filed: Jun. 22, 2010

(65) Prior Publication Data

US 2011/0151402 A1 Jun. 23, 2011

(30) Foreign Application Priority Data

Dec. 18, 2009 (KR) .......................... 10-2009-0126589

(51) Int. Cl.
*B67D 7/78* (2010.01)
(52) U.S. Cl.
USPC ............... 222/145.6; 222/153.01; 222/153.04
(58) Field of Classification Search
CPC .................... B05C 17/00553; B05C 17/00506
USPC .............. 222/145.5, 145.6, 137, 459, 153.01, 222/153.04; 239/304, 414, 402, 336; 366/181.5
See application file for complete search history.

(56) References Cited

U.S. PATENT DOCUMENTS

| 4,538,920 | A | * | 9/1985 | Drake | .......................... | 366/181.5 |
| 5,413,253 | A |   | 5/1995 | Simmen | | |
| 6,398,761 | B1 | * | 6/2002 | Bills et al. | ...................... | 604/191 |
| 7,997,450 | B2 | * | 8/2011 | Heusser et al. | ............. | 222/145.6 |
| 8,007,164 | B2 | * | 8/2011 | Miyano et al. | .............. | 366/173.1 |
| 8,074,843 | B2 | * | 12/2011 | Keller | ............................ | 222/137 |
| 8,100,295 | B2 | * | 1/2012 | Keller | ............................ | 222/137 |
| 8,147,122 | B2 | * | 4/2012 | Pieroni | ...................... | 366/171.1 |
| 2002/0145007 | A1 | * | 10/2002 | Sawhney et al. | .............. | 222/137 |
| 2008/0029542 | A1 |   | 2/2008 | Keller | | |
| 2009/0152300 | A1 | * | 6/2009 | Hayman et al. | ............. | 222/145.6 |

FOREIGN PATENT DOCUMENTS

DE 202006014087 12/2006
EP 1125641 8/2001

\* cited by examiner

*Primary Examiner* — Paul R Durand
*Assistant Examiner* — Jeremy W Carroll
(74) *Attorney, Agent, or Firm* — Jordan and Hamburg LLP (57) ABSTRACT

In a mixing tip of an impression material cartridge, a top connective plate is on the center of the top of a pair of cylinders, with an impression material cartridge installed with the connecting end of each of a pair of mixing tips facing each other located on each side of the top connective plate, and a mixing screw inserted into a protruding mixing tube on the center of the upper part, with a connective structure of the mixing tips having protruding connecting wings on the lower side of the supporting structure, formed to achieve diagonal symmetry of a rotational bump on the end surface of the connecting wings on a lower supporting side of the mixing tips, and on the lower surface of the rotational bump, cylindrical guide pins that guide the connecting direction of the mixing tips are each formed to protrude towards the bottom.

1 Claim, 7 Drawing Sheets

STRUCTURE FOR CONNECTING A MIXING TIP TO AN IMPRESSION CARTRIDGE

DETAILED EXPLANATION OF THE INVENTION

1. Technological Field

This invention is based on the mixing tip connective structure of the impression material cartridge, which in detail allows for easy and simple connection with the impression material cartridge in no relation to the connecting direction of the mixing tip, to exponentially improve the convenience in use, as well as to maintain a strong and stabilized connective state, structured with a mixing tip connective structure of the impression material cartridge, completely preventing an impression material leak caused by the loosening of the mixing tip at use.

2. Technological Background

To acquire the dental impression at a dentist, a dental impression material of a mixture of liquid silicon base and a hardener is generally used, which are stored in a pair of joined cylindrical tubes that each contains the liquid silicon base and hardener, which can be ejaculated simultaneously for the convenience of use. Traditional impression material cartridges have been used as on FIG. 1 or FIG. 3, furnished as a pair of cylinder (23)(24), connected to the lower connective flange (22), with a top connective plate (25) on the upper central area of the aforesaid cylindrical pair (23)(24), and connective ejaculatory stations (23a)(24a) are each protruding on the upper surface of the cylinder (23)(24) of the aforesaid top connective plate (25), with mixing tip connective ends (27)(28) installed facing each other on the internal lower side of the rotational connective grooves (27a)(28a) on each sides of the aforesaid top connective plate (25), and a positioning groove (27b) on the upper central area on the aforesaid unilateral mixing tip connective end (27).

Figure 1:
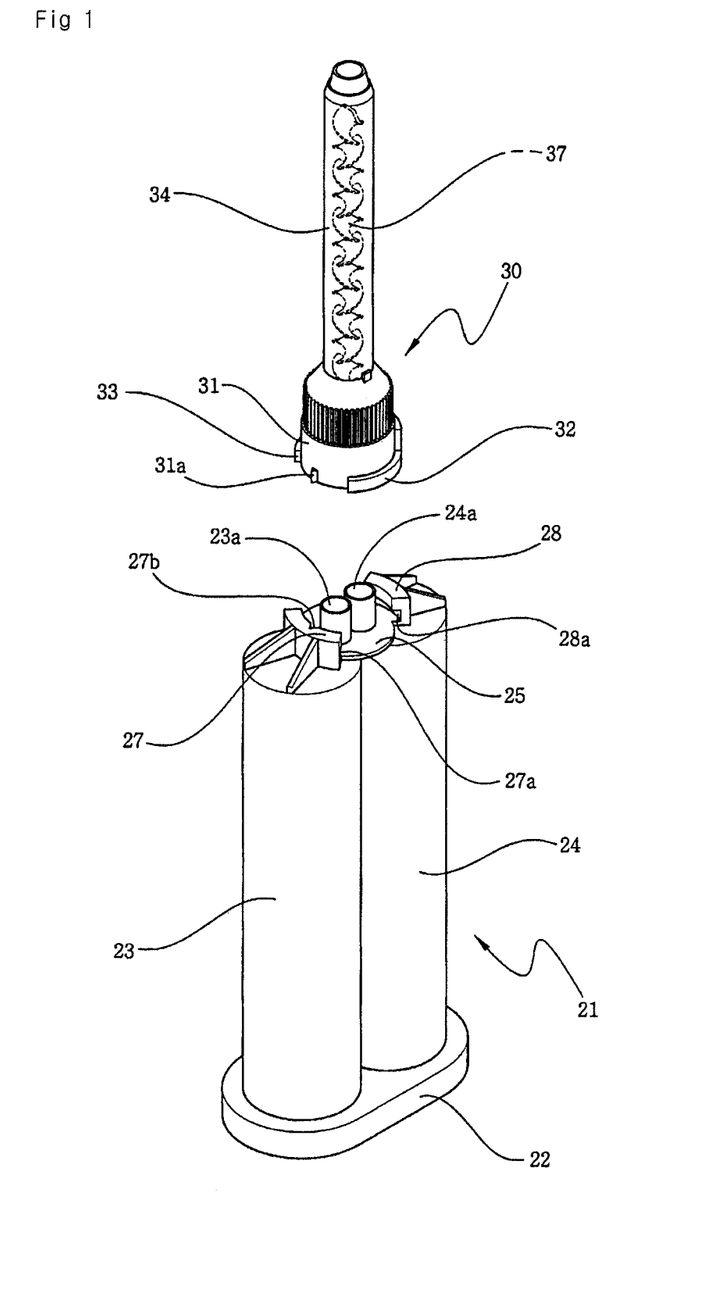
FIG. 1 is a slanted view of the exploded view of the traditional impression material cartridge and mixing tip (A)(B) of FIG. 2 is the frontal view of the connective process of the traditional impression material cartridge and mixing tip.
Figure 3:
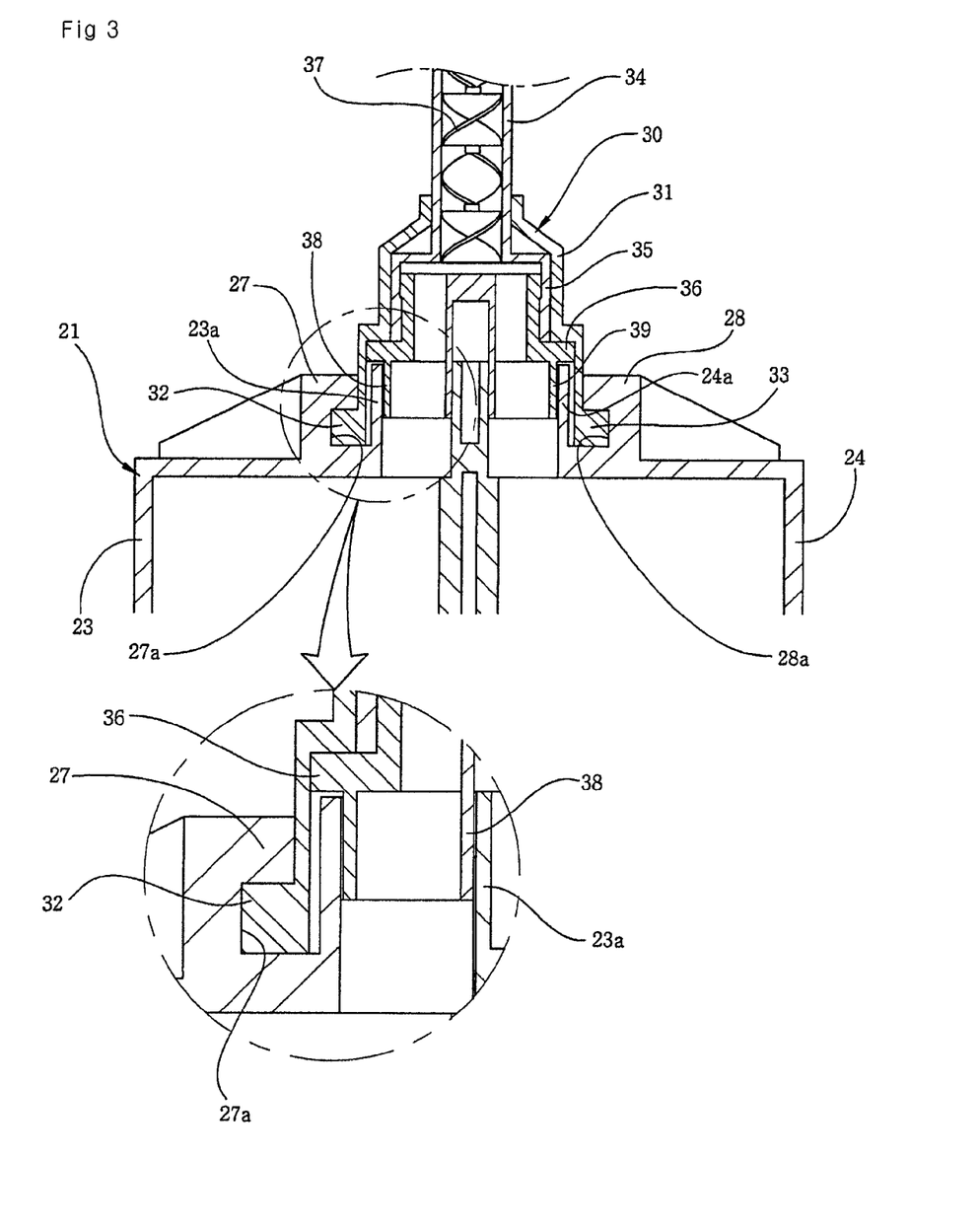
FIG. 3 is the cross-sectional view of the connective process of the traditional impression material cartridge and mixing tip.

The traditional impression material cartridge (21) structured as such, has a connective mixing tip (30) that mixes the simultaneously ejaculated silicon base and hardener each stored in one cylinder of the pair (23)(24), and as the connective mixing tip (30) on the traditional impression material cartridge (21) that is shown on FIG. 1 or FIG. 3, the rotationally connecting connective wings (32)(33) are each protruded on the rotational connecting grooves (27a)(28a) of the mixing tip connective ends (27)(28) of lower sides of the aforesaid impression material cartridge (21). Between the aforesaid connecting wings (32)(33), a protruding cap group (31) is furnished with a positioning bump (31a) inserted through the positioning groove (27b) formed on the mixing tip connective ends (27) of the aforesaid impression material cartridge (21), with a mixing tube (34) protruding on the inserting tube (35) that is installed as an insert on the upper central side of the inside of the aforesaid cap group (31), and on upper central side of the inside of the aforesaid inserting tube (35), a mixing screw (37) protrudes and is inserted into the aforesaid mixing tube (34), with connecting tubes (38)(39) that each connect the ejaculating tubes (23a)(24a) of the aforesaid impression material cartridge (21) on the lower part, protruding on a downward direction, collectively structured to be installed as the connective connector (36).

Figure 2:
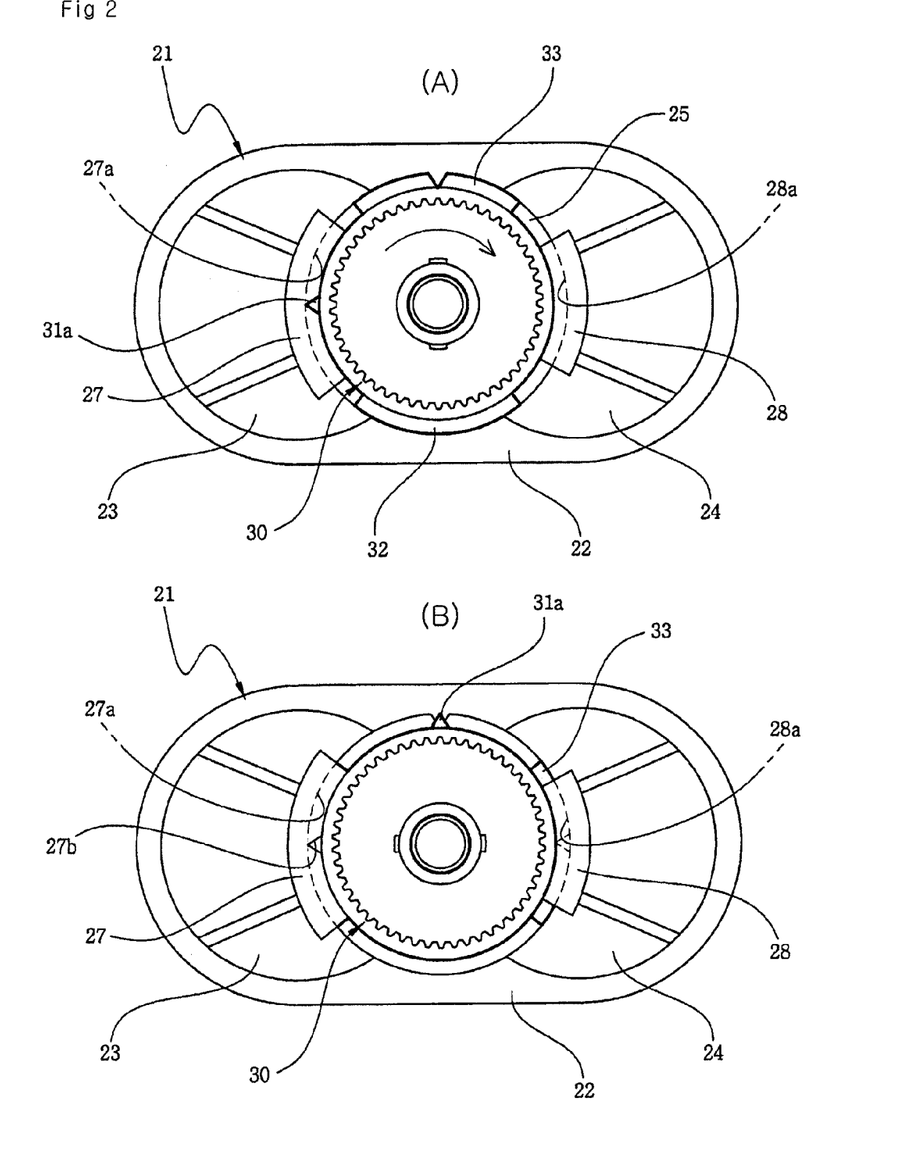

Structured in this manner, as the traditional impression material cartridge (21) and the mixing tip (30) are seen on (A) of FIG. 2, the mixing tip (30) is stabilized on the top connective plate (25) of the impression material cartridge (21) so that the positioning bump (31a) formed on the cap group (31) of the mixing tip (30) may be inserted in the positioning groove (27b) formed on the mixing tip connective ends (27) of the impression material cartridge (21), after which the stabilized mixing tip (30) as it is shown on (B) of FIG. 2 is rotated clockwise, and the connecting wings (32)(33) formed on the lower sides of the cap group (31) of the mixing tip (30) are each inserted to be connected to the rotational connective grooves (27a)(28a) of the mixing tip connective ends (27)(28) of the impression material cartridge (21).

However, the traditional impression cartridge structured in the aforesaid manner and the connective structure of the mixing tip had to be positioned in a specific connecting direction according to the positioning groove (27b) on the mixing tip connective ends (27) of the impression material cartridge (21) and the positioning bump (31a) formed on the cap group (31) of the mixing tip (30), in the case of connection with the mixing tip (30) on the impression material cartridge, which created an uncomfortable and inconvenient use.

Furthermore, following the varied width of the mixing tip connective ends (27)(28) installed to be facing in opposite directions of the top connective plate (25) of the impression material cartridge (21) of the traditional impression material cartridge and the connective structure of the mixing tip, a difference in the contact area between the connective wings (32)(33) of the mixing tip (30) and the mixing tip connective ends (27)(28) of the impression material cartridge (21) is formed, being indifferent in the connective strength joining the connecting wings (32)(33) on each side of the cap group (31) of the mixing tip (30), thus creating a leakage of the impression material on the side with weak connectivity in case of excessive ejaculatory pressure on the impression material cartridge (21).

Also, as the traditional impression material cartridge and connective structure of the mixing tip is displayed on FIG. 3, the insertion of the connecting tubes (38)(39) protruding downwards on the lower side of the connective connector (36), which has been inserted on the inside of the mixing tip (30) on the ejaculatory tubes (23a)(24a) formed on the top surface of the top connective plate (25) of the impression material cartridge (21) to connect the mixing tip (30) to the impression material cartridge (21), causes a small gap between the external surface of the connective tubes (38)(39) and the internal surface of the ejaculatory tubes (23a)(24a) based on the allowance for assembly; thus creating the problem of leakage of the impression material through this gap when excessive ejaculatory pressure is added on the impression material cartridge.

In addition, the connective structure of the traditional impression material cartridge and the mixing tip is formed to connect the connecting wings (32)(33), which are formed on the lower side of the cap group (31) of the mixing tip (30), rotating clockwise to each be inserted in the rotational connective groove (27a)(28a) of the mixing connective ends (27)(28) of the impression material cartridge (21), thus creating the problem of leakage of impression material as the connective state is easily dismantled at pressure on the mixing tip (30).

CONTENT OF THE INVENTION

Task to be Resolved

This invention was created for the resolution of aforesaid problems, being created with a top connective plate on the upper central part of a pair of cylinders, with an impression material cartridge installed to face in opposing directions of the mixing connective ends on each side of the top connective plate, and a protruding mixing tube that has a mixing screw inserted on its upper central area. And regarding the connective structure of the mixing tip formed with connecting wings protruding on the lower sides, the rotational bump is formed on a diagonal symmetry on the end surfaces of the connecting wings on the lower sides of the aforesaid mixing tip, with cylindrical guide pins protruding downwards that guide the connective direction of the mixing tip on the lower surface of the aforesaid rotational bump. And on each top surfaces of the top connective plate of the aforesaid impression material cartridge, a protruding guiding plate for connecting the mixing tip is structured as a diagonal symmetry of a straight guide pin inserting strip and a curved guide pin guider, which together in detail allows for easy and simple connection with the impression material cartridge in no relation to the connecting direction of the mixing tip, to exponentially improve the convenience in use, as well as to maintain a strong and stabilized connective state, structured with a mixing tip connective structure of the impression material cartridge, completely preventing an impression material leak caused by the loosening of the mixing tip at use—which is the technological task to be resolved.

Measure for the Resolution of the Task

The invention to achieve the aforesaid technological task, is formed of a top connective plate on the top central side of a pair of cylinders with the lower parts connected by connective flanges, and on the upper surface of the aforesaid top connective plate, a connective socket that has ejaculatory holes that each connect to the cylinders protrudes, and on the sides of the aforesaid top connective plates, mixing connective ends installed to face in opposing directions of each other, each formed with rotational connective grooves on its lower internal part, collectively structured as the impression material cartridge, and a mixing tube with a mixing screw inserted within it is formed on the top central side. And regarding the connective structure of the mixing tip that is structured to be installed with a connective connector formed by a connective tube to protrude downwards, with ejaculatory holes on the connective socket of the aforesaid impression material cartridge on the inside of the cap group formed to protrude connective wings that rotationally connect on the rotational connective groove of the mixing tip connective ends of the impression material cartridge, when the connecting wings on the end surfaces of the connecting wings formed on the cap group for the aforesaid mixing tip rotationally connects to the rotational connective groove of the mixing tip connective ends of the impression material cartridge, the rotational bumps that are caught on the side surfaces of the mixing tip connective ends are formed on a diagonal symmetry. And on the lower surface of the aforesaid rotational bump, cylindrical guide pins that guide the connective direction of the mixing tip protrudes downwards, and on either side of the top connective plate formed on the aforesaid impression material cartridge, a straight guide pin insertion strip and curve guide pin guider are formed on a diagonal symmetry on the mixing tip connective guiding plate protruding as a feature of the invention.

Furthermore, this invention is formed with an internal environment of the ejaculatory hole in the form of a taper that narrows as it goes down, on the connective socket of the aforesaid impression material cartridge, and the connective tube of the connective connector that is inserted on the inside of the cap group of the aforesaid mixing tip, narrows as it goes down, which is formed as a feature of this invention.

Effect

Based on the mixing tip connective structure of the impression material cartridge of this invention, which is structured as mentioned, allows for easy and simple connection with the impression material cartridge in no relation to the connecting direction of the mixing tip, to exponentially improve the convenience in use, as well as to maintain a strong and stabilized connective state, structured with a mixing tip connective structure of the impression material cartridge, completely preventing an impression material leak caused by the loosening of the mixing tip at use, as the effect of this invention.

BRIEF ACCOUNT OF THE FIG

(A)(B) of FIG. 5 is the frontal view of the impression material cartridge and mixing tip based on this invention.

(A)(B) of FIG. 6 is the frontal view of the connective process of the impression material cartridge and mixing tip based on this invention.

DESCRIPTION OF FIGURES ON THE KEY SECTIONS OF THE DRAWINGS

| | |
|---|---|
| 1: Impression Material Cartridge | 2: Connective Flange |
| 3, 4: Cylinder | 5: Top Connective Plate |
| 6: Connective Socket | 6a, 6b: Ejaculatory Holes |
| 7, 8: Mixing Tip Connective Ends | 7a, 8a: Rotational Connective Grooves |
| 9: Mixing Tip Connective Guiding Plate | 10a, 10b: Guide Pin Insertion Strips |
| 11a, 11b: Guide Pin Guiding Curves | 12a, 12b: Guide Pin Connective Grooves |
| 13: Mixing Tip | 14: Mixing Screw |
| 15: Mixing Tube | 16, 17: Connective Wings |
| 16a, 17a: Rotational Bumps | 16b, 17b: Guide Pins |
| 19: Cap Group | 19: Connective Connector |
| 19a, 19b: Connective Tubes | |

DETAILS FOR THE IMPLEMENTATION OF THE INVENTION

Explaining this invention in detail referring to FIG. 4 or FIG. 7 to achieve the aforesaid goal is as follows.

Figure 4:
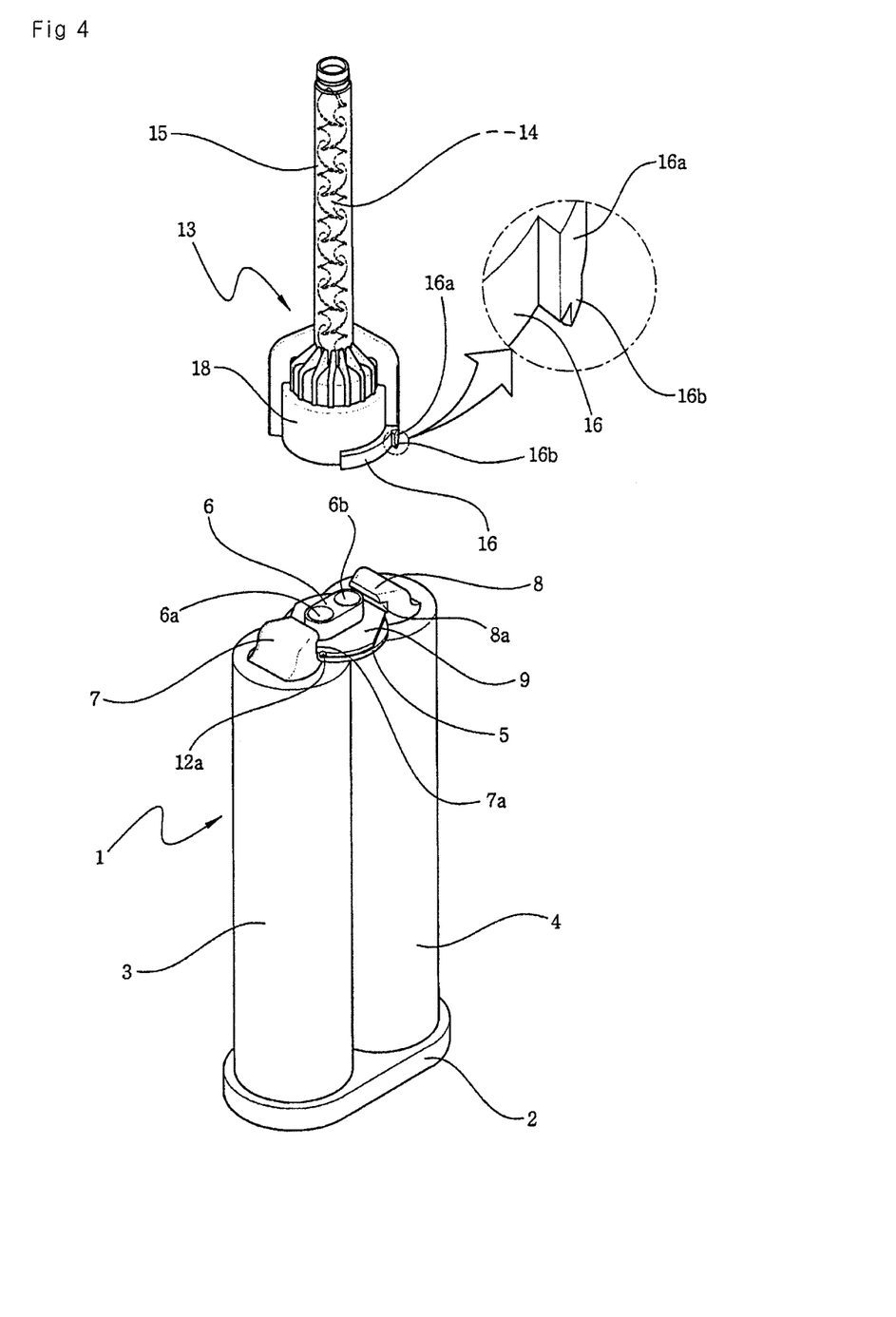
FIG. 4 is the slanted view of the exploded view of the impression material cartridge and mixing tip based on this invention.
Figure 5:
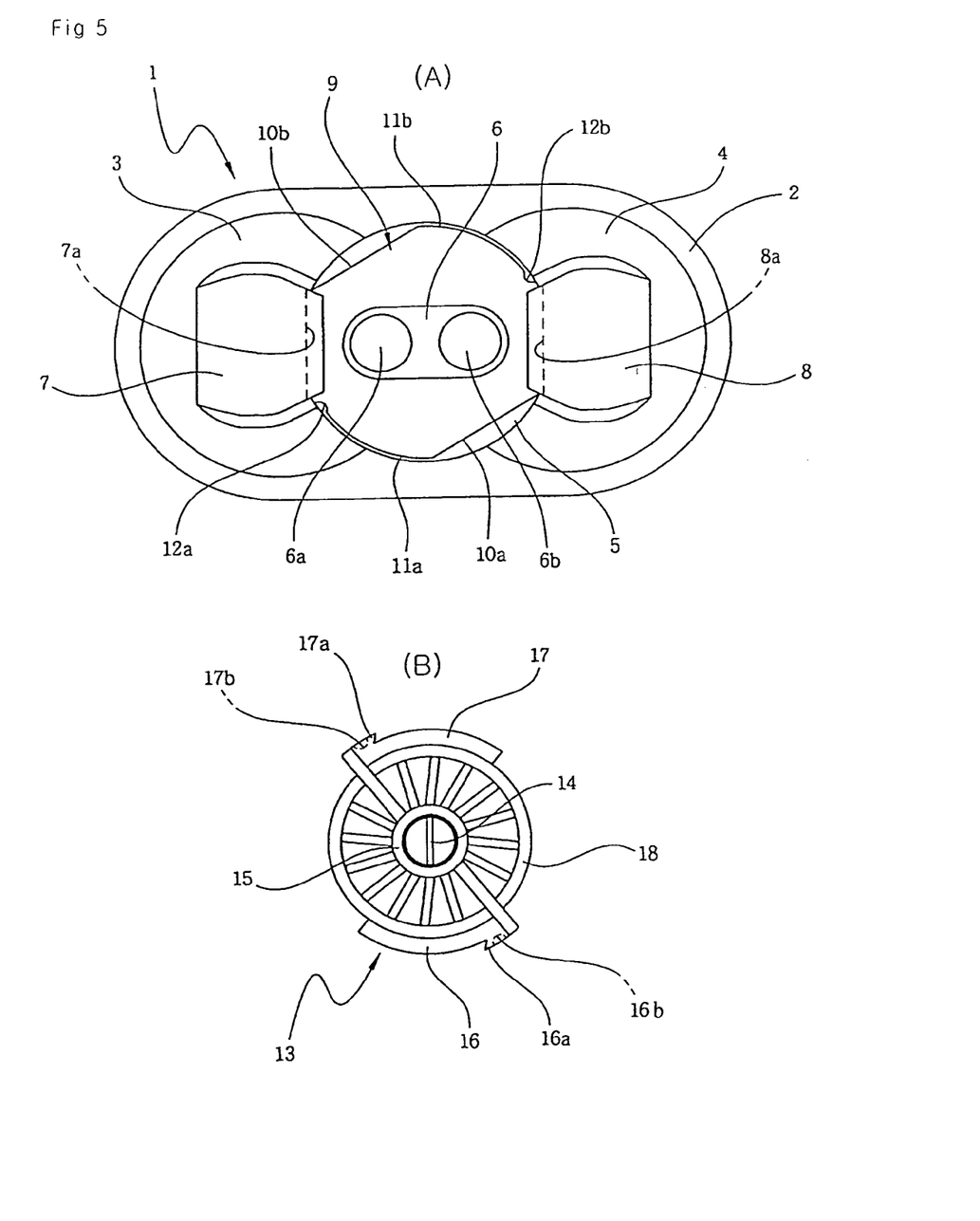
Figure 6:
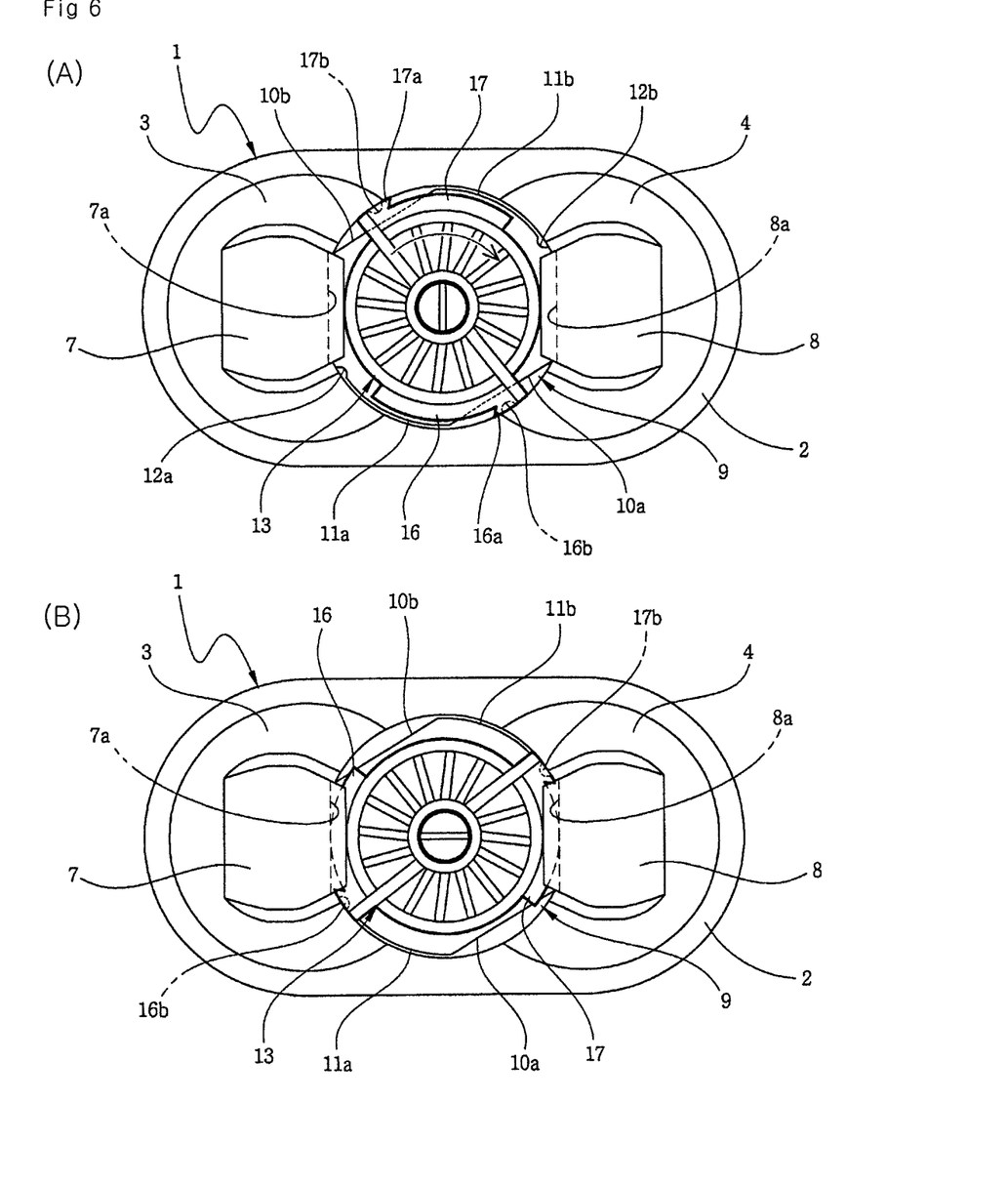
Figure 7:
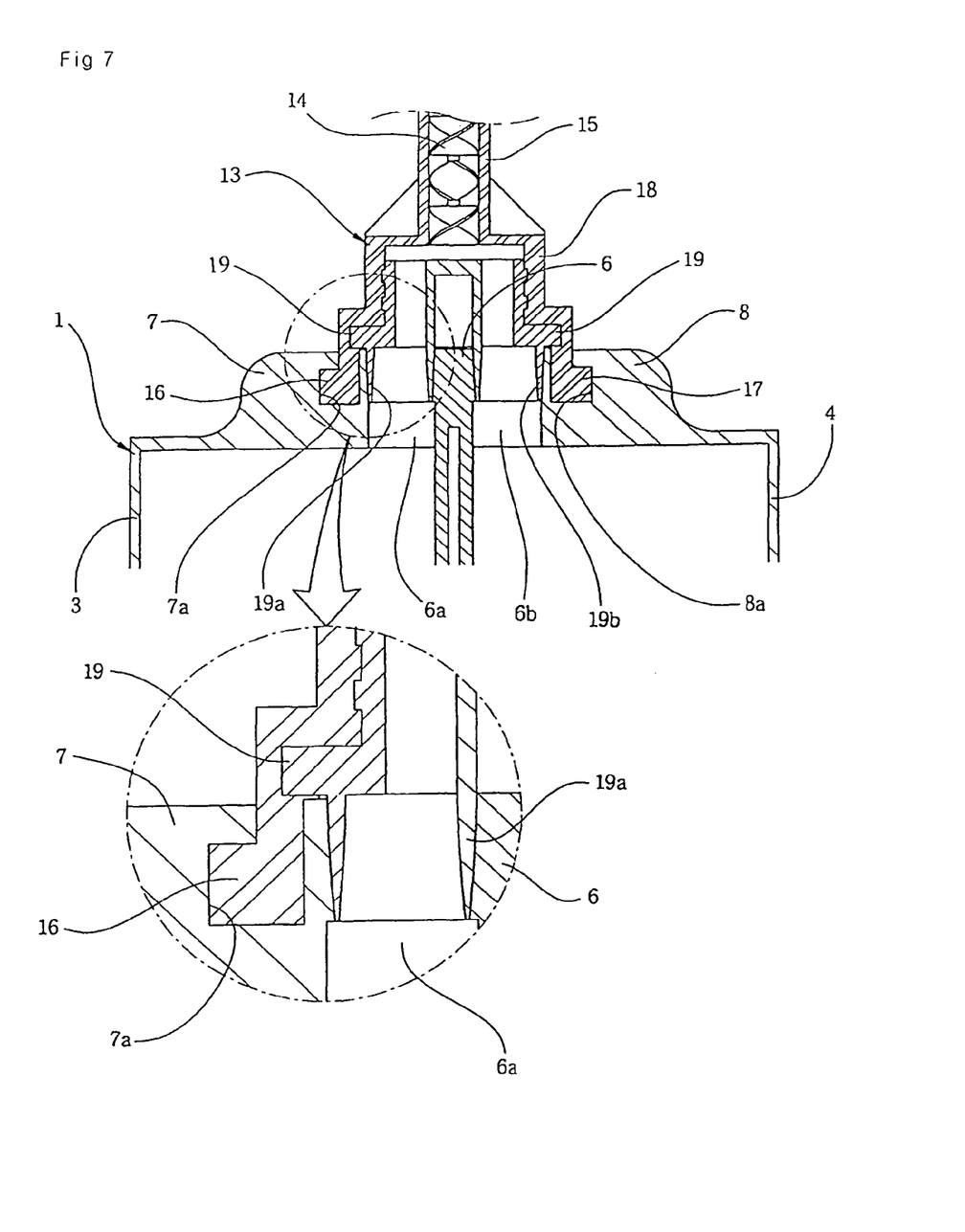
FIG. 7 is the cross-sectional view of the connective process of the impression material cartridge and mixing tip based on this invention.

FIG. 4 shows the slanted exploded view of the impression material cartridge and mixing tip based on this invention, (A)(B) of FIG. 5 displays a frontal view of the impression material cartridge and mixing tip based on this invention, (A)(B) of FIG. 6 is the frontal view of the connecting process of the impression material cartridge and mixing tip based on this invention, and FIG. 7 is the cross-section of the connecting process of the impression material cartridge and mixing tip based on this invention.

As seen on FIG. 4 or FIG. 7, the impression material cartridge based on this invention has a top connective plate on the upper central side of the pair of cylinder (3)(4), with its based connected by connective flanges (2). On the top surface of the aforesaid top connective plate (5), a protruding connective socket (6) that has ejaculatory holes (6a)(6b) each inserted into the cylinders (3)(4) is formed, with mixing tip connective ends (7)(8) installed facing in opposing directions of each other that have rotational connective grooves (7a)(8a) on the lower internal part, located on each side of the aforesaid top connective plate (5). On the top sides of the aforesaid top connective plate (5), straight guide pin insertions (10a)(10b), guide pin guiding curves (11a)(11b), and guide pin connective grooves (12a)(12b) are formed at diagonal symmetry on the protruding mixing tip connective guiding plate (9).

Here, it is suitable to form a uniform width so that the mixing tip connective ends (7)(8) installed on an opposing direction of the aforesaid top connective plate (5) may be connected based on the contact area indifferent from the connective wings (16)(17) of the mixing tip (13).

When the width of the aforesaid mixing tip connective ends (7)(8) are uniform as this, a uniform connective strength is applied on the connective wings (16)(17) formed on each side of the cap group (18) of the mixing tip (13) following the connectivity of the uniform contact area of the connective wings (16)(17) of the mixing tip (13) and the mixing tip connective ends (7)(8) of the impression material cartridge (1), thus completely preventing the leakage of impression material through areas of weak connectivity even at excessive ejaculatory pressure on the impression material cartridge (1).

Also, it is suitable to form the upper internal environment of the ejaculatory holes (6a)(6b) formed on the connective socket (6) of the aforesaid impression material cartridge (1), in a form of a taper, narrowing down.

When the upper internal environment of the ejaculatory holes (6a)(6b) of the aforesaid connective socket (6) is formed as this, in the case of insertion of connective tubes (19a)(19b) of the connective connector (19) installed on the inside of the mixing tip (13), in the ejaculatory tubes (6a)(6b) formed on the connective socket (6) of the impression material cartridge (1) for the connection of the mixing tip (13) on the impression material cartridge (1), a small gap based on the external side of the connective tubes (19a)(19b) and the internal side of the ejaculatory holes (6a)(6b) based on the allowance for assembly is not formed at all, following the sturdy adhesion of the ends of the connective tubes (19a)(19b) on the upper internal sides of the ejaculatory holes (6a)(6b), thus completely preventing the leakage of impression material through this gap at excessive ejaculatory pressure on the impression material cartridge (1).

On the other hand, as the mixing tip is connected on the impression material cartridge based on this invention shown on FIG. 4 or FIG. 7, a mixing screw (14) inserted into the protruding mixing tube (15) on the center of the upper part is formed, with a cap group (18) furnished with protruding connecting wings (16)(17) that rotationally connects on the rotational connective groove (7a)(8a) of the mixing connective ends (7)(8) of the aforesaid impression material cartridge (1) on the lower supporting side, and on the end surface of the aforesaid connecting wings (16)(17) of the aforesaid cap group (18), the connecting wings (16)(17) rotationally connect with the rotational connecting groove (7a)(8a) of the mixing tip connecting end (7)(8) of the impression material cartridge (1), with the rotational bumps (16a)(17a) on the side of the mixing tip connective ends (7)(8) form diagonal symmetry. On the lower surface of the aforesaid rotational bumps (16a)(17a), cylindrical guide pins (16b)(17b) that guide the connective direction of the mixing tip (13) protrudes downwards, and on the internal sides of the aforesaid cap group (18) ejaculatory holes (6a)(6b) on the connective socket (6) of the aforesaid impression material cartridge (1) each connecting to connective tubes (19a)(19b) protruding downwards installed within a connective connector (19).

At which point, the connecting tubes (19a)(19b) of the connective connector (19) installed on the inside of the cap group (19) of the aforesaid mixing tip (13), is suited when it narrows as it goes down.

When the connective tubes (19a)(19b) of the aforesaid connective connector (19) is formed with a narrower bottom as this, during the insertion of the connective tubes (19a)(19b) of the connective connector (19) installed on the inside of the mixing tip (13) into the ejaculatory holes (6a)(6b) formed on the connective socket (6) of the impression material cartridge (1) for the connection of the mixing tip (13) with the impression material cartridge (1), the ends of the connective tubes (19a)(19b) is not only easy to insert within the ejaculatory holes (6a)(6b), but following the stable adhesion of the ends of the connective tubes (19a)(19b) on the upper internal sides of the ejaculatory holes (6a)(6b), there are no small gaps created by the allowance for assembly between the external side of the connective tubes (19a)(19b) and the internal side of the ejaculatory tubes (6a)(6b), thus completely preventing the leakage of impression material through this gap at excessive ejaculatory pressure on the impression material cartridge (1).

The explanation of the mixing tip connective structure of the impression material cartridge based on this invention, structured as mentioned, is as follows.

In the case of connecting the mixing tip to the impression material cartridge based on this invention, firstly as it is displayed on (A) of FIG. 6, the end surfaces of the connective wings (16)(17) formed on the lower support of the mixing tip (13) is formed at a diagonal symmetry on the rotational bumps (16a)(17a), with cylindrical guide pins (16b)(17b) formed on its lower surface, each being inserted in the area formed on the upper sides of the top connective plate (5) based on the guide pin insertion strips (10a)(10b) formed on each side of the mixing tip connective guiding plate (9) of the impression material cartridge (1), with the mixing tip (13) being stabilized on the top connective plate (5) of the impression material cartridge (1) for this purpose.

Here, as the aforesaid mixing tip is displayed on (A) of FIG. 6, when the connective wings (16)(17) are inserted to be located between the mixing tip connective ends (7)(8) of the impression material cartridge (1), the cylindrical guide pins (16b)(17b) formed on the mixing tip (13) is inserted and stabilized on the area formed on the upper sides of the top connective plate (5) based on the guide pin insertion strips (10a)(10b) on the sides of the mixing tip connective guiding plate (9) of the impression material cartridge (1), thus making connection on the impression material cartridge (1) more easy and simple with no regards to the connective direction.

Subsequently, when the stabilized mixing tip (13) on the top connective plate (5) of the aforesaid impression material cartridge (1) is rotated clockwise, the connective wings (16) (17) formed on the lower end of the mixing tip (13) as seen on (B) of FIG. 6, are each rotationally connected on the rotational grooves (7a)(8a) formed on the mixing connective ends (7)(8) of the impression material cartridge (1), and the cylindrical guide pins (16b)(17b), formed on the lower surface of the rotational bumps (16a)(17a) formed to achieve diagonal symmetry on the end surfaces of the connective wings (16)(17) on the low support of the mixing tip (13), are guided by the guide pin guiding curves (11a)(11b) formed on the sides of the mixing tip connective guiding plate (9), to be each connected on the guide pin connective groove (12a)(12b).

Here, the mixing tip (13) that is connected to the aforesaid impression material cartridge (1), is connected with the rotational connective grooves (7a)(8a) on the mixing tip connective ends (7)(8) of the impression material cartridge 91) based on the connecting wings (16)(17), and at the same time connecting to the guide pin connective grooves (12a)(12b) on the sides of the mixing tip connective guiding plate (9) based on the cylindrical guide pins (16b)(17b), maintaining a sturdy stabilization of the connective state, thus effectively preventing the leakage of impression material caused by the loosening of the mixing tip (13).

Furthermore, when the mixing tip is to be connected to the impression material cartridge based on this invention, the connective tubes (19a)(19b) of the connective connector (19) installed on the insides of the mixing tip (13) is inserted within the ejaculatory holes (6a)(6b) on the connective socket (6) of the impression material cartridge (1), as shown on FIG. 7.

At this stage, the connective tubes (19a)(19b) of the aforesaid connective connector (19) is formed with a width that narrows down to the bottom, and with the ejaculatory holes (6a)(6b) of the aforesaid connective socket (6) following the taper form of the top internal sides, the ends of the connective tubes (19a)(19b) are not only easily inserted into the ejaculatory holes (6a)(6b), but the ends of the connective tubes (19a)(19b) are more stably adhered to the upper internal sides of the ejaculatory holes (6a)(6b), creating no small gap based on the allowance for assembly between the external sides of the connective tubes (19a)(19b) and the internal sides of the ejaculatory tubes (6a)(6b), thus completely preventing the leakage of impression material through this gap at excessive ejaculatory pressure on the impression material cartridge (1).

Based on the mixing tip connective structure of the impression material cartridge of this invention, which is structured as mentioned, allows for easy and simple connection with the impression material cartridge in no relation to the connecting direction of the mixing tip, to exponentially improve the convenience in use, as well as to maintain a strong and stabilized connective state, structured with a mixing tip connective structure of the impression material cartridge, completely preventing an impression material leak caused by the loosening of the mixing tip at use, as the effect of this invention.

The invention claimed is:

1. A structure for connecting a mixing tip to an impression material cartridge in which the impression material cartridge comprises
    a top connective plate formed on an upper central part of a pair of cylinders that are connected at bottom portions of the cylinders by a connective flange, and on a top surface of the top connective plate a connective socket is provided with ejaculatory holes that each connect to the cylinders; and
    at opposing sides of the top connective plate are mixing tip connective ends, the mixing tip connective ends are each formed with rotational connective grooves on an internal lower part of the mixing tip connective ends and are installed to face in opposing directions; the structure further comprising
    on a top central part of the structure, a mixing tube for the insertion of a mixing screw protrudes, and on a lower part of the structure, a connective structure of a mixing tip installed with a connective connector is formed with connective tubes that protrude downwards, each connective tube being connected with the ejaculatory holes on the connective socket of the impression material cartridge on an inside of the mixing tip and on protruding connective wings that each rotationally connect on the rotational connective grooves of the mixing tip connective ends of the impression material cartridge; and
    when the connective wings rotationally connect with the rotational connective grooves of the mixing tip connective ends of the impression material cartridge, on an end surface of the connective wings on the mixing tip, rotational bumps extending from the connective wings and which are positioned on sides of the mixing tip connective ends each form diagonal symmetry; and
    on a lower surface of the rotational bumps, cylindrical guide pins that guide the connective direction of the mixing tip are formed to be protruded downwards so as to extend downwardly from the rotational bumps and beneath lowermost end portions of the end surface of the connective wings and the rotational bumps; and
    on the sides of the top connective plate, a mixing tip connective guiding plate protrudes with diagonally symmetrical guide pin insertion strips disposed diagonally across from each other, guide pin guiding curves, and guide pin connective grooves, each of the guide pin insertion strips, guide pin guiding curves and guide pin connective grooves being formed along a side surface of the mixing tip connective guiding plate, the guide pin guiding curves and the guide pin connective grooves each comprising an arcuate configuration along said side surface of the mixing tip connective guiding plate so as to guide the cylindrical guide pins to connection with the guide pin connective grooves so that said cylindrical guide pins seat within and thereagainst said guide pin connective grooves upon connection of the mixing tip with the impression material cartridge; and
    upper internal surfaces of the ejaculatory holes on the connective socket of the impression material cartridge have an internal diameter formed in a taper format so as to narrow toward the mixing tip, and the connective tubes of the connective connector are formed with a width that narrows toward the cylinders,
    in which upon connection of the mixing tip to the impression material cartridge, portions of the connective connector and connective tubes thereof surroundingly seat directly atop, alongside and within portions of the ejaculatory holes such that portions of the mixing tip connective ends are disposed therebetween each of the connective connector and connective tubes thereof and the connective wings.

* * * * *